(12) United States Patent
Evitt et al.

(10) Patent No.: US 7,858,830 B2
(45) Date of Patent: Dec. 28, 2010

(54) PROCESS FOR RECOVERING PHENOL FROM A BPA WASTE STREAM

(75) Inventors: Steven Evitt, Somerville, MA (US); Chung-Ming Chi, Needham, MA (US); Marshall S. Lee, Concord, MA (US); David Palmer, Katy, TX (US)

(73) Assignee: Badger Licensing LLC, Cambridge, MA (US)

( * ) Notice: Subject to any disclaimer, the term of this patent is extended or adjusted under 35 U.S.C. 154(b) by 137 days.

(21) Appl. No.: 12/259,841

(22) Filed: Oct. 28, 2008

(65) Prior Publication Data

US 2010/0105960 A1    Apr. 29, 2010

(51) Int. Cl.
*C07C 37/74* (2006.01)
*C07C 37/20* (2006.01)

(52) U.S. Cl. ...................... 568/749; 568/728

(58) Field of Classification Search ................ 568/728, 568/749–756
See application file for complete search history.

(56) References Cited

U.S. PATENT DOCUMENTS

| | | | |
|---|---|---|---|
| 3,466,337 A | 9/1969 | Smith et al. | |
| 4,131,749 A | 12/1978 | Kiedik et al. | |
| 6,133,486 A | 10/2000 | Maas et al. | |
| 6,303,835 B1 | 10/2001 | Shafer et al. | |
| 6,459,004 B1 | 10/2002 | Ono et al. | |
| 7,301,056 B2 * | 11/2007 | Prein et al. | 568/749 |

FOREIGN PATENT DOCUMENTS

| | | |
|---|---|---|
| EP | 0110937 A1 | 6/1984 |
| WO | 00/40531 A1 | 7/2000 |
| WO | 2007/044139 | 4/2007 |

OTHER PUBLICATIONS

International Search Report mailed Jun. 2, 2010 in the related application PCT/US09/59973.

* cited by examiner

*Primary Examiner*—Brian J Davis
(74) *Attorney, Agent, or Firm*—Peter W. Roberts, Esq.; Roberts Mlotkowski Safran & Cole, P.C.

(57) ABSTRACT

An improved process for recovering phenol from a bisphenol-A residue stream by reconfiguring the distillation column and the cracking reactor in a way that separates the reboil/distillation heat load and the cracking heat load, so that separate heat sources are used.

23 Claims, 5 Drawing Sheets

PROCESS FOR RECOVERING PHENOL FROM A BPA WASTE STREAM

FIELD

This invention is directed to a process for recovering phenol from a bisphenol-A waste stream and in particular to a process in which the cost efficiency of the phenol recovery is increased by using steam of a minimum value to meet the duty cycle of each of the process steps.

BACKGROUND

Bisphenol-A (4,4'-dihydroxy-2,2-diphenylpropane or BPA) is produced by condensation of acetone with an excess of phenol in the presence of an acidic catalyst or a cation-exchange resin. The crude product, in addition to the desired bisphenol-A and unreacted phenol, contains unwanted by-products, such as bisphenol-A isomers, trisphenols and other higher molecular weight materials. The bisphenol-A is normally separated from the crude product by a single or a series of crystallization steps, leaving a mother liquor stream enriched in unwanted by-products, a portion of which stream is removed to purge unwanted by-products from the process. Alternately, the bisphenol-A may be separated from the crude product by a single or series of distillation steps, which also creates a stream enriched in unwanted by-products, a portion of which is removed. The removed stream may contain unreacted phenol and bisphenol-A as well as the unwanted by-products. Phenol is typically recovered from the removed stream by distillation, normally vacuum distillation.

In order to increase recovery of phenol for recycle into the BPA process, it is known to catalytically crack the unwanted by-products, many of which contain phenol-moieties within their structures. Typically, the products of the cracking step are recycled into a distillation step, where the heat from the cracking process helps to provide the heat input required by the distillation step and the phenol liberated in the cracking step is recovered. The products of the cracking step are typically phenol or a combination of phenol and isopropenyl phenol (IPP). In this process, the system uses the cracking heat source to supply both the cracking heat duty and the distillation column reboiler duty required for phenol recovery. U.S. Pat. No. 6,459,004 to Ono et al. discloses such a system (col. 2, lines 31-36).

However, the distillation step does not require as high a temperature as the cracking reaction, but the reboil heat duty required to recover the products of the cracking step is substantially higher than the heat duty required for cracking. The result is that a higher quality (higher temperature) and therefore higher cost heat source is used to supply a much larger heat duty than is required, which is not economically efficient.

SUMMARY

In one embodiment, the present invention is directed to a process for recovering phenol from a BPA waste stream, the process comprising:

(a) feeding a BPA waste stream comprising phenol moiety-containing aromatic compounds to a distillation column;

(b) distilling said waste stream in said distillation column to form a phenol-containing distillate product stream and a column bottoms stream;

(c) feeding a major portion of said column bottoms stream to a low temperature utility, heating said major portion to a first temperature and recycling said heated major portion to the distillation column;

(d) feeding a minor portion of said column bottoms stream to a high temperature utility and heating said minor portion to a cracking temperature which is higher than said first temperature;

(e) feeding said heated minor portion to a catalytic cracking vessel; and (f) cracking and flashing said minor portion to form a phenol-rich effluent stream and a phenol-poor residue stream.

The process can further comprise recycling at least a portion of said phenol-poor residue stream to said high temperature utility.

Advantageously, the first temperature and the flow of said major portion of heated column bottoms are controlled to provide the heat required for the distillation column heat duty.

Conveniently, a portion of the phenol-poor residue stream is fed to a heat-exchanger, which is used to pre-heat said minor portion of said column bottoms upstream of said high temperature utility.

The process can further comprise refluxing said phenol-rich effluent stream in a rectification unit mounted on said catalytic cracking vessel, and said phenol-rich effluent stream can be recycled to said distillation column.

In this embodiment, the refluxing stream is taken from said BPA waste stream, or taken from said phenol effluent stream, or taken from a side stream from said distillation column.

In some situations, it is advantageous that the refluxed phenol-rich effluent stream is condensed and recovered.

Conveniently, the catalytic cracking vessel can be mounted below and in the same shell as said distillation column, said distillation column and said cracking vessel are separated by a trap-out tray, and said minor portion of said column bottoms overflows the trap and falls into said cracking vessel, prior to step (d).

Typically, the BPA waste stream comprises BPA isomers, unreacted phenol, trisphenols, hydroxyphenyl chromans, isopropenyl phenol dimers, and indanes.

In another embodiment, the present invention is directed to a process of producing bisphenol-A (BPA), the process comprising:

(a) condensing acetone with a molar excess of phenol in the presence of a catalyst under conditions to produce an effluent stream comprising BPA isomers, unreacted phenol, trisphenols, hydroxyphenyl chromans, isopropenyl phenol dimers, and indanes;

(b) recovering BPA and unreacted phenol from said effluent stream to leave a BPA waste stream comprising BPA isomers, unrecovered phenol, trisphenols, hydroxyphenyl chromans, isopropenyl phenol dimers, indanes and other heavier aromatic compounds;

(c) feeding said BPA waste stream to a distillation column;

(d) distilling said waste stream in said distillation column to form a phenol-containing distillate effluent stream and a heavier column bottoms stream;

(e) feeding a major portion of said column bottoms stream to a low temperature utility, heating said major portion to a first temperature and recycling said heated major portion to the distillation column;

(f) feeding a minor portion of said column bottoms stream to a high temperature utility and heating said minor portion to a cracking temperature which is higher than said first temperature;

(g) feeding said heated minor portion to a catalytic cracking vessel; and (h) cracking said minor portion to form a phenol-rich effluent stream and a phenol-poor residue stream.

The process can further comprise recycling at least a portion of said phenol-poor residue stream to said high temperature utility.

Advantageously, in this embodiment of the process, the first temperature and the flow of said major portion of heated column bottoms are controlled to provide the heat required for the distillation column heat duty.

Conveniently, in this embodiment of the process, a portion of the phenol-poor residue stream is fed to a heat-exchanger, which is used to pre-heat said minor portion of said column bottoms upstream of said high temperature utility.

The process can further comprise a step wherein the phenol-rich effluent stream is recycled to said distillation column.

Alternatively, the process can further comprise refluxing said phenol-rich effluent stream in a rectification unit mounted on said catalytic cracking vessel, wherein the refluxing stream is taken from said BPA waste stream, or from said phenol effluent stream, or even from said distillation column.

In one embodiment, the refluxed phenol-rich effluent stream is condensed and recovered.

Conveniently, the catalytic cracking vessel can be mounted below and in the same shell as said distillation column, said distillation column and said cracking vessel are separated by a trap-out tray, and said minor portion of said column bottoms overflows the trap and falls into said cracking vessel, prior to step (f).

DETAILED DESCRIPTION

Figure 1:
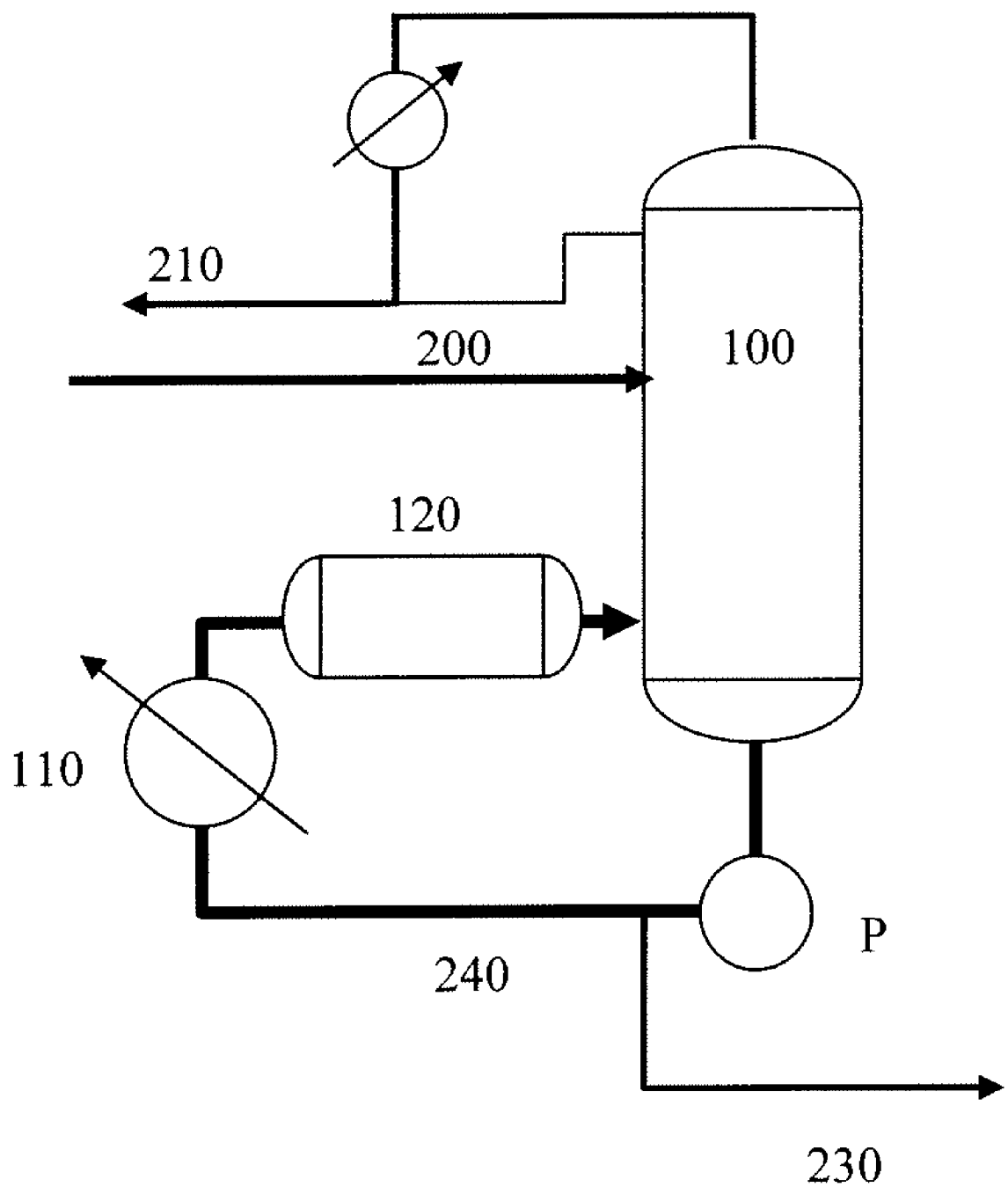
FIG. 1 illustrates a conventional prior art cracking and distillation process.

The bisphenol-A (BPA) synthesis method initially involves reacting acetone with a stoichiometric excess of phenol in the presence of an acid catalyst. The phenol/acetone molar ratio is usually in the range from 3 to 30, typically from 5 to 20. The reaction is carried out at a temperature of usually from 50 to 100° C. under a pressure of usually from atmospheric pressure to 600 kPa.

As the catalyst, usually strong mineral acids or strongly acidic cation exchange resins such as sulfonic acid type resins, including those partially neutralized with a sulfur-containing amine compound are used. As the sulfur-containing amine compound, ordinary promoters used for the synthesis of bisphenol-A such as, for example, 2-(4-pyridyl)ethanethiol, 2-mercaptoethylamine, 3-mercaptopropylamine, N,N-dimethyl-3-mercaptopropylamine, N,N-di-n-butyl-4-mercaptobutylamine, and 2,2-dimethylthiazolidine can be used. Such a promoter is used in an amount of usually 2 to 30 mol %, such as 5 to 20 mol % based on the acid group (sulfonic group) in the acid ion exchanger.

The condensation reaction of the phenol and acetone is typically conducted in a fixed bed continuous flow system or a suspended bed batch system. In the case of the fixed bed flow system, the liquid space velocity of the mixture of the raw materials supplied to the reactor is usually 0.2 to 50 hr$^{-1}$. In the case of the suspended bed batch system, the amount of the strongly acid ion exchange resin used, although variable depending on the reaction temperature and pressure, is usually 20 to 100% by weight based on the mixture of the raw materials. The reaction time is usually 0.5 to 5 hours.

In addition to the desired bisphenol-A, the effluent from the condensation reaction comprises reaction-generated water, unreacted acetone, unreacted phenol, and a variety unwanted by-products containing phenol-moieties, such as bisphenol-A isomers (for example, 2-(4-hydroxyphenyl)-2-(2-hydroxyphenyl)propane or o,p-BPA), trisphenol (see formula I below), isopropenyl phenol (IPP) dimers (see formulae IIa, IIb and IIc below) and hydroxyphenyl chromans (see formulae IIIa and IIIb below), substituted xanthenes and more highly condensed compounds having three or more phenyl rings in the molecular framework. Collectively, the IPP dimers, hydroxylphenyl chromans, indanes, xanthenes and more highly condensed compounds are termed as "BPA heavies."

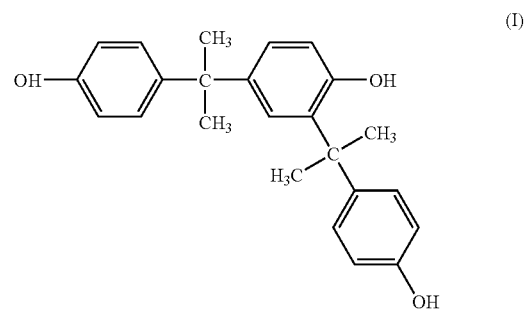

(I)

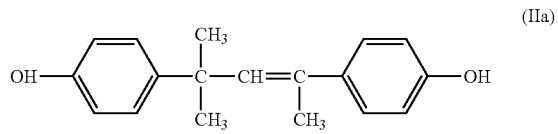

(IIa)

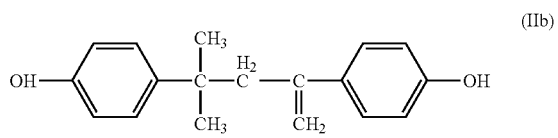

(IIb)

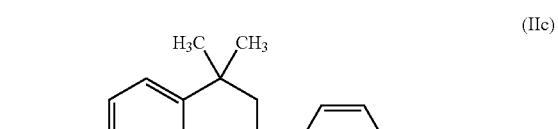

(IIc)

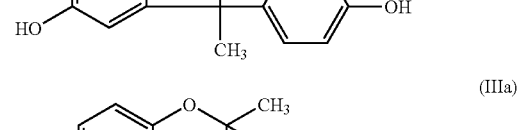

(IIIa)

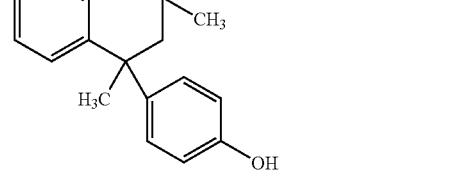

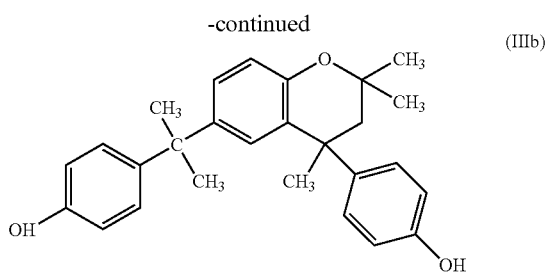

(IIIb)

These by-products, as well as the water, phenol and acetone, impair the suitability of the BPA for the production of polymers and must be separated from the condensation effluent. For the production of polycarbonate in particular, high demands are made on the purity of the raw material BPA.

The purification of the BPA is carried out by a multi-stage cascade of suitable purification processes such as, for example, suspension crystallization, melt crystallization, distillation and/or desorption. After separation of the BPA product, these processes leave a mother liquor or BPA waste stream, which contains BPA, water, unreacted phenol and possibly unreacted acetone, and which is rich in the above-mentioned phenol-moiety containing aromatic by-products. Typically, this stream of mother liquor is recycled to the condensation reaction. In order to maintain the catalytic activity of the acidic ion exchanger, all or some of the water that has formed is removed beforehand by distillation, together with any unreacted acetone that is still present. The dewatered mother liquor so obtained is supplemented with additional phenol and acetone and fed back into the condensation unit.

Such a recycle procedure has the disadvantage that the by-products of the BPA preparation become concentrated in the circulating stream and can adversely affect the purity of the final BPA product and may lead to deactivation of the catalyst system. In order to avoid excessive concentration of the by-products in the circulating stream, a portion of the mother liquor mixture must be discharged from the system. The discharge is typically effected by removing a portion of the mother liquor from the circulating stream, often after distillation to remove water of reaction, unreacted acetone and part of the unreacted phenol. The composition of the mother liquor at this point, and accordingly also the composition of the discharge, typically comprises from 60 to 90 wt. % phenol, from 6 to 18 wt. % BPA and from 3 to 15 wt. % BPA isomers and heavier by-products. Since this discharge stream contains significant quantities of phenol and other useful products, the discharge is a valuable process stream which is subjected to further processing.

Further processing of the discharge stream can involve distilling off the phenol to a residual content of less than 20 wt. %, such as less than 10 wt. %, especially less than 5 wt. %, even less than 1 wt. %, normally by vacuum distillation, leaving a heavy residue stream comprising <10 wt. % phenol, from 15 to 85 wt. % BPA and from 15 to 85 wt. % by-products, which residue stream must be removed from the process.

Advantageously, further processing of the discharge stream can be conducted, such as subjecting the bisphenol-A isomers, trisphenols and other high molecular weight components in the discharge stream to thermal or catalytic cracking to generate phenol and isopropenylphenol (IPP) for enhanced recovery. The cracking step may be subsequent to or coincident with phenol recovery by distillation. A suitable cracking process is described in International Patent Publication No. WO 2007/044139, the entire contents of which are incorporated herein by reference.

The products of the cracking step can be recycled to the phenol recovery distillation step, where the heat from the cracking step helps to provide the heat input required by the distillation step, and the phenol liberated in the cracking step is recovered. Typically, the cracking heater also serves to provide the heat duty required by the distillation column. However, the distillation step does not require as high a temperature as the cracking reaction, but the heat duty required to recover the products of the cracking step is substantially higher than the heat duty required for cracking. The result is that a higher quality (higher temperature) and therefore higher cost heat source is used to supply a much larger heat duty than is required, which is not economically efficient.

FIG. 1 illustrates a conventional prior art cracking and distillation process, wherein a BPA waste stream 200 is directed into a phenol recovery distillation column 100, which acts to recover a phenol-containing product stream 210, which is then recycled into the BPA condensation reactor (not shown). A bottoms stream 240 from the distillation column 100 is directed through pump P, from which the stream 240 is sent to a heater/reboiler 110, where it is heated to cracking temperature by a high temperature utility, such as by high temperature steam. A small portion of the bottoms stream 230 is sent off site for other uses and/or disposal. The heated stream 240 is sent into a cracking reactor 120 where it is cracked to produce phenol, which is then sent back into distillation column 100. In this conventional process, the flow of stream 240 is controlled so that the total heat input in heater/reboiler 110 is equal to the heat duty required by the distillation column 100 plus the heat duty required for cracking.

According to the improved process of the present application, the present inventors have recognized that two distinctly different heat loads are involved in the process; the heat duty necessary to recover phenol by distillation, and the heat duty required to promote the cracking reaction. The larger of the two heat loads, that to recover the phenol, can be satisfied using a lower value heat source, since the temperature necessary for phenol distillation and recovery is significantly lower than that required for cracking of the bottoms stream. Therefore, significant cost savings can be realized by reconfiguring the distillation column and the cracking reactor in a way that separates the reboil/distillation heat load and the cracking heat load, so that separate heat sources are used.

FIGS. 2 to 5 illustrate various ways of separating the phenol recovery heat duty (the reboil duty) from the cracking heat duty, but should not be construed as the only ways to practice the present invention.

Figure 2:
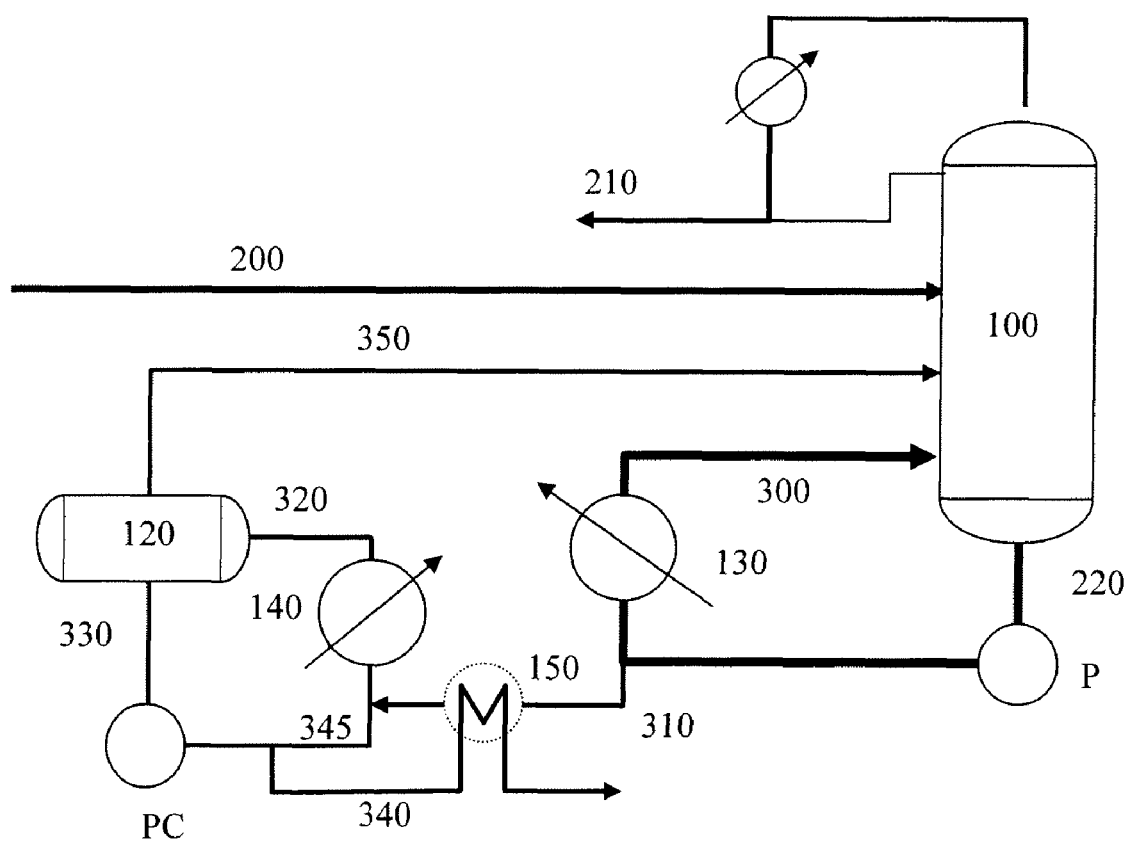
FIG. 2 illustrates a first embodiment of the improved process of the present invention, wherein the heat duties for column distillation and cracking are separated.

In the embodiment of FIG. 2, a column bottoms stream 220 is taken from distillation column 100, through pump P, where a major portion 300 of the stream, is directed through reboiler 130, where it is heated to a first temperature with a low temperature utility, sufficient to provide the heat duty necessary for the distillation column. The flow of stream 300 is regulated so that the reboiler 130 provides the required reboiler duty. A minor portion 310 of the column bottoms, stream, is directed through a cracking feed effluent heater 150, where heat is recovered from a fraction of the final cracker product, stream 340. Stream 340, is sent off for other uses or for disposal to purge unrecoverable impurities from the process. Stream 310 is then fed into a cracking loop comprising a cracking heater 140, catalytic cracking flash vessel 120 and recycle pump PC. Stream 310 is fed into cracking heater 140, where it is brought up to cracking temperature, which is higher than said first temperature, by a high temperature utility (i.e. high temperature steam), and then the heated stream 320 flows into cracking flash vessel 120, where it is cracked to produce a phenol-rich stream 350, which flows back into distillation column 100. The temperature and pressure of the cracking flash vessel 120 are adjusted to maintain a very high phenol purity in the cracked vapor stream 350. The bottoms stream 330 from the cracking flash vessel, which is a phenol-poor stream, goes to the cracking product recycle pump PC, after which a small product stream fraction 340 is split from a larger cracking recycle stream fraction 345. The product stream fraction 340 is supplied to the heater 150 to preheat column 100 bottoms portion 310, whereas the recycle stream fraction 345 is returned to cracking reboiler 140.

Figure 3:
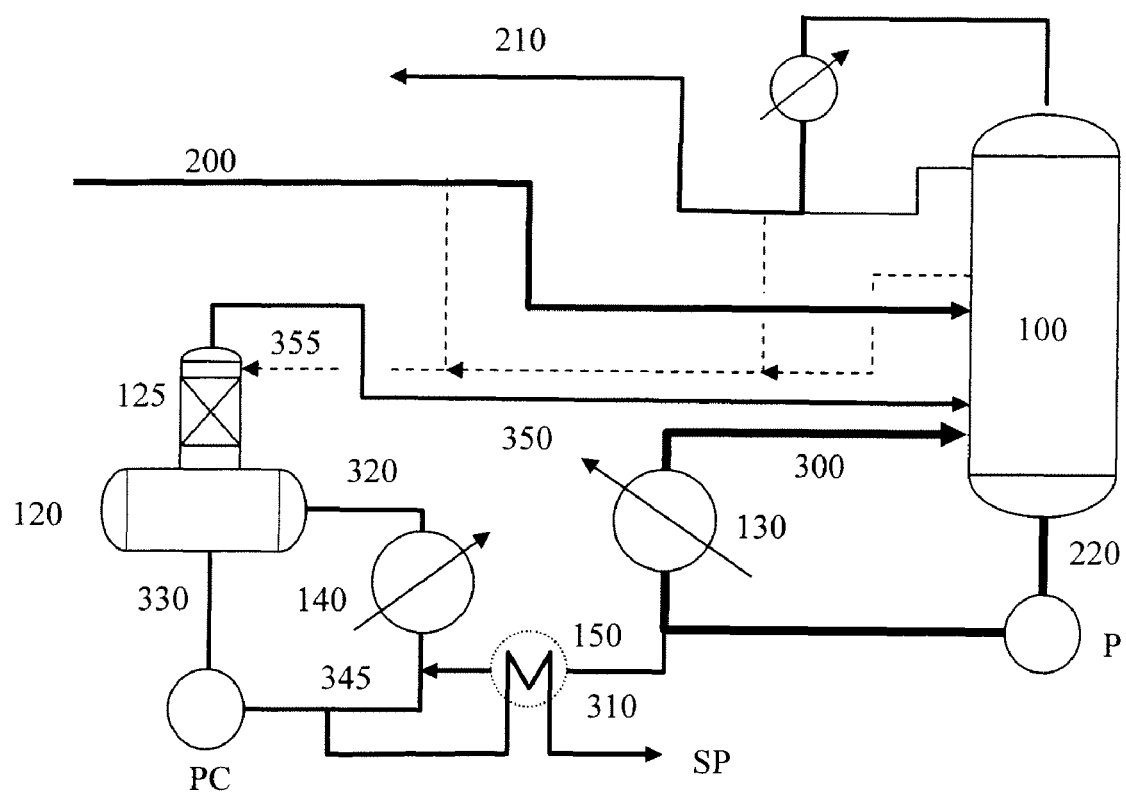
FIG. 3 illustrates a second embodiment of the improved process of the present invention, which is a modification of the process of FIG. 2.

FIG. 3 is a variation of the process of FIG. 2, wherein a small rectification unit 125 is added to cracking flash vessel 120. The rectification unit 125 can be refluxed with a stream 355 taken from any or all of column feed stream 200, a side draw from distillation column 100, or from phenol recycle stream 210. The addition of the rectifying section permits operation of the cracking flash vessel at more severe conditions, e.g. at a higher temperature or lower pressure, while maintaining a high phenol purity in the phenol-rich cracked vapor stream 350, which is recycled to distillation column 100.

Figure 4:
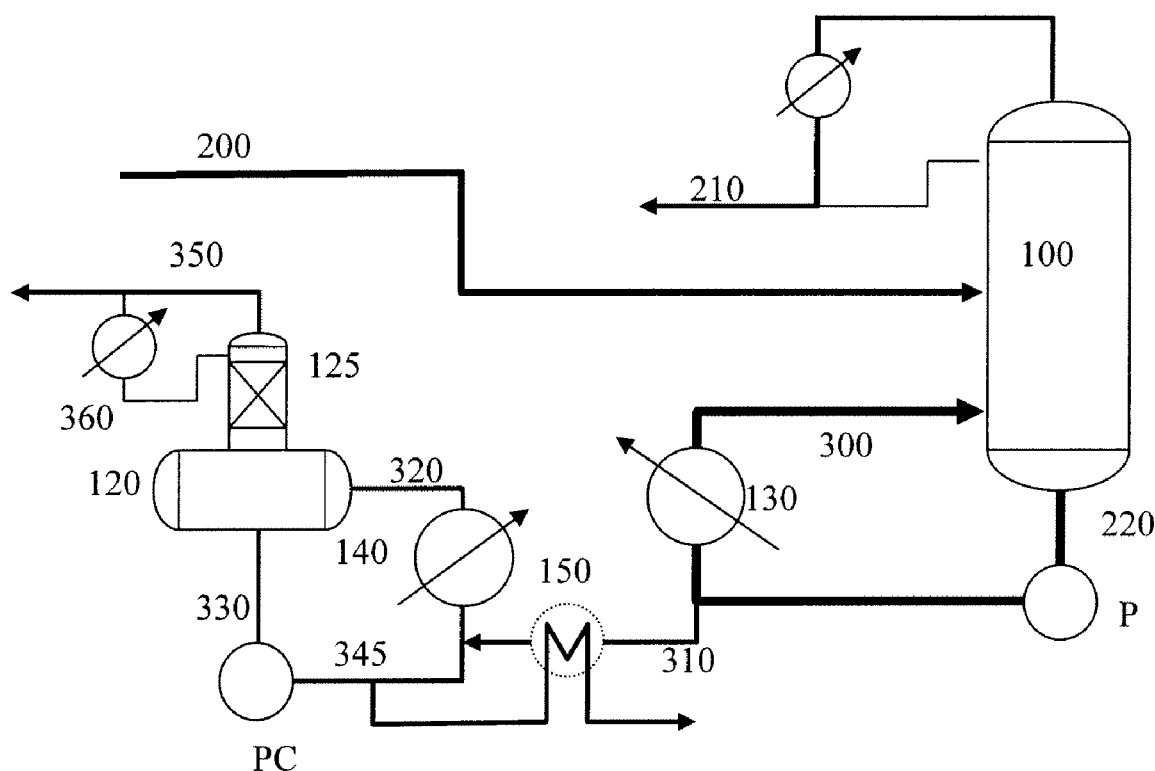
FIG. 4 illustrates a modification of the process of FIG. 3.

FIG. 4 illustrates a further modification of the process of FIG. 3, wherein the phenol-rich cracked vapor stream 350 is almost totally condensed, most of which is taken off as recycle phenol product, while a small portion 360 is used to reflux the rectification section 125. This arrangement is useful where the improved process is being added to an existing facility and the existing phenol recovery distillation column 100 is limited in capacity.

Figure 5:
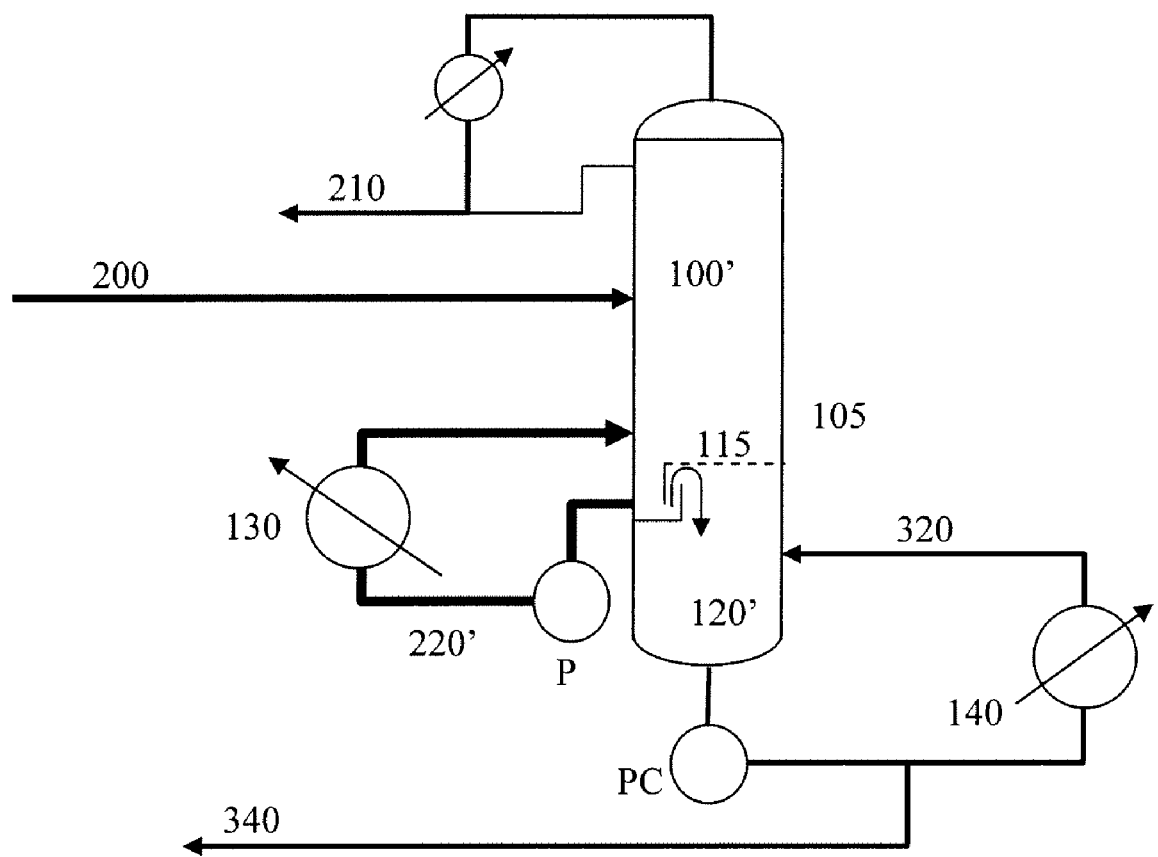
FIG. 5 illustrates a further embodiment of the present invention, wherein a distillation column and cracking reactor are combined in a single shell.

In FIG. 5, the phenol recovery distillation column 100' and the cracking reactor 120' are combined into one shell 105 and separated by a trap-out tray 115. The liquid from the bottom of the distillation column 100' is collected and the majority, stream 220', is sent by pump P to reboiler 130, where it is heated by a low temperature utility to provide the reboil duty. A minor portion of the liquid from the bottom of the distillation column 100' overflows the trap and falls into the cracking vessel 120', from where it is directed by cracking recycle pump PC into cracking reboiler 140 to be heated to cracking temperature by a high temperature utility. The heated stream 320 is then sent into cracking vessel 120' to be cracked, and the phenol-rich vapor resulting from the cracking step flows up into the distillation column 100'. Similarly to the previous embodiments, a small portion of the final cracker effluent, stream 340, is sent off for other uses or for disposal. Stream 340 can also be used for heating the feed stream 200 to the distillation column 100', While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for recovering phenol from a BPA waste stream, comprising:
   (a) feeding a BPA waste stream comprising phenol moiety-containing aromatic compounds to a distillation column;
   (b) distilling said waste stream in said distillation column to form a phenol-containing distillate product stream and a column bottoms stream;
   (c) feeding a first portion of said bottoms stream to a low temperature utility, heating said first portion to a first temperature and recycling said heated first portion to the distillation column;
   (d) feeding a second portion of said column bottoms stream to a high temperature utility and heating said second portion to a cracking temperature which is higher than said first temperature;
   (e) feeding said heated second portion to a catalytic cracking vessel; and
   (f) cracking and flashing said second portion to form a phenol-rich effluent stream and a phenol-poor residue stream.

2. The process of claim 1, further comprising recycling at least a portion of said phenol-poor residue stream to said high temperature utility.

3. The process of claim 1, wherein the first temperature and the flow of said first portion of heated column bottoms are controlled to provide the heat required for the distillation column heat duty.

4. The process of claim 1, wherein a portion of the phenol-poor residue stream is fed to a heat-exchanger, which is used to pre-heat said second portion of said column bottoms upstream of said high temperature utility.

5. The process of claim 1, wherein said phenol-rich effluent stream is recycled to said distillation column.

6. The process of claim 1, further comprising refluxing said phenol-rich effluent stream in a rectification unit mounted on said catalytic cracking vessel.

7. The process of claim 6, wherein a refluxing stream is taken from said BPA waste stream.

8. The process of claim 6, wherein a refluxing stream is taken from said phenol effluent stream.

9. The process of claim 6, wherein a refluxing stream is taken from a side stream from said distillation column.

10. The process of claim 6, wherein said refluxed phenol-rich effluent stream is condensed and recovered.

11. The process of claim 1, wherein said catalytic cracking vessel is mounted below and in the same shell as said distillation column, said distillation column and said cracking vessel are separated by a trap-out tray, and said second portion of said column bottoms overflows the trap and falls into said cracking vessel, prior to step (d).

12. The process of claim 1, wherein said BPA waste stream comprises BPA isomers, unreacted phenol, trisphenols, hydroxyphenyl chromans, isopropenyl phenol dimers, and indanes.

13. A process of producing bisphenol-A (BPA), comprising:
   (a) condensing acetone with a molar excess of phenol in the presence of a catalyst under conditions to produce an effluent stream comprising BPA isomers, unreacted phenol, trisphenols, hydroxyphenyl chromans, isopropenyl phenol dimers, and indanes;
   (b) recovering BPA and unreacted phenol from said effluent stream to leave a BPA waste stream comprising BPA isomers, unrecovered phenol, trisphenols, hydroxyphenyl chromans, isopropenyl phenol dimers, indanes and other heavier aromatic compounds;
   (c) feeding said BPA waste stream to a distillation column;
   (d) distilling said waste stream in said distillation column to form a phenol-containing effluent stream and a heavier column bottoms stream;
   (e) feeding a first portion of said bottoms stream to a low temperature utility, heating said first portion to a first temperature and recycling said heated first portion to the distillation column;

(f) feeding a second portion of said column bottoms stream to a high temperature utility and heating said second portion to a cracking temperature which is higher than said first temperature;

(g) feeding said heated second portion to a catalytic cracking vessel; and (h) cracking said second portion to form a phenol-rich effluent stream and a phenol-poor residue stream.

14. The process of claim 13, further comprising recycling at least a portion of said phenol-poor residue stream to said high temperature utility.

15. The process of claim 13, wherein the first temperature and the flow of said first portion of heated column bottoms are controlled to provide the heat required for the distillation column heat duty.

16. The process of claim 13, wherein a portion of the phenol-poor residue stream is fed to a heat-exchanger, which is used to pre-heat said second portion of said column bottoms upstream of said high temperature utility.

17. The process of claim 13, wherein said phenol-rich effluent stream is recycled to said distillation column.

18. The process of claim 13, further comprising refluxing said phenol-rich effluent stream in a rectification unit mounted on said catalytic cracking vessel.

19. The process of claim 18, wherein a refluxing stream is taken from said BPA waste stream.

20. The process of claim 18, wherein a refluxing stream is taken from said phenol effluent stream.

21. The process of claim 18, wherein a refluxing stream is taken from a side stream from said distillation column.

22. The process of claim 18, wherein said refluxed phenol-rich effluent stream is condensed and recovered.

23. The process of claim 13, wherein said catalytic cracking vessel is mounted below and in the same shell as said distillation column, said distillation column and said cracking vessel are separated by a trap-out tray, and said second portion of said column bottoms overflows the trap and falls into said cracking vessel, prior to step (f).

* * * * *